United States Patent [19]

Acton et al.

[11] Patent Number: 4,826,964

[45] Date of Patent: *May 2, 1989

[54] BRIDGED OXYGEN ANALOGS OF DAUNORUBCIN AND DOXORUBICIN

[75] Inventors: Edward M. Acton, Houston, Tex.; George L. Tong, Cupertino, Calif.

[73] Assignee: SRI International, Menlo Park, Calif.

[*] The portion of the term of this patent subsequent to Apr. 29, 2003, has been disclaimed.

[21] Appl. No.: 856,678

[22] Filed: Apr. 25, 1986

Related U.S. Application Data

[63] Continuation-in-part of Ser. No. 598,016, Apr. 9, 1984, Pat. No. 4,585,859, which is a continuation-in-part of Ser. No. 496,122, May 24, 1983, Pat. No. 4,464,529, which is a continuation-in-part of Ser. No. 400,120, Jul. 20, 1982, abandoned.

[51] Int. Cl.$^4$ .............................. C07H 15/24
[52] U.S. Cl. ..................................... 536/6.4
[58] Field of Search ........................... 536/6.4; 514/34

[56] References Cited

U.S. PATENT DOCUMENTS

| | | | |
|---|---|---|---|
| 4,035,566 | 5/1977 | Israel et al. | 536/4 |
| 4,109,076 | 9/1978 | Henry et al. | 536/6.4 |
| 4,202,967 | 5/1980 | Tong et al. | 536/17 A |
| 4,301,277 | 11/1981 | Acton et al. | 536/6.4 |
| 4,314,054 | 2/1982 | Acton et al. | 536/17 A |
| 4,464,529 | 8/1984 | Mosher et al. | 536/6.4 |
| 4,585,859 | 4/1986 | Mosher et al. | 536/6.4 |

OTHER PUBLICATIONS

Henry (1976), "Adriamycin", *ACS Symposium Series, No. 30, Cancer Chemotherapy,* American Chemical Society 15-57.
Arcamone (1981), "Doxorubicin", *Acadamic Press,* 17:163-355.
Acton et al, (1981), *J. Med. Chem.,* 24:669.
Tong et al, (1979), *J. Med. Chem.,* 22:912-918.
Acton et al, (1984), *J. Med. Chem.,* 27:638.

*Primary Examiner*—Ronald W. Griffin
*Assistant Examiner*—Elli Peselev
*Attorney, Agent, or Firm*—Irell & Manella

[57] ABSTRACT

Compounds of the formula

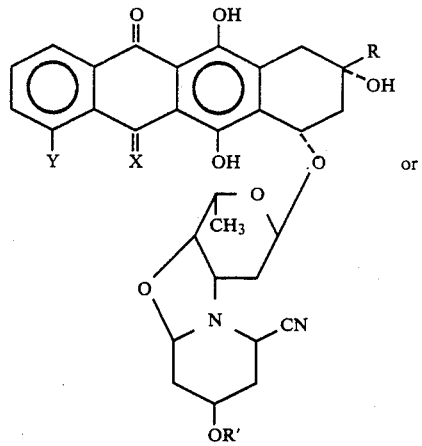

or

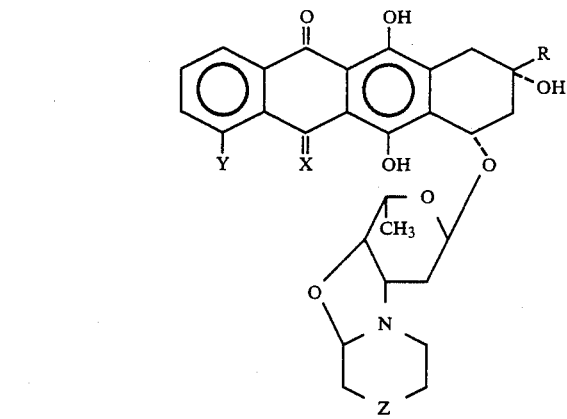

wherein
R is —COCH$_3$, —CHOHCH$_3$, —COCH$_2$OH, or —CHOHCH$_2$OH; hydrogen; hydroxyl; a 1 to 3 carbon alkyl; a 1 to 3 carbon ω-hydroxyalkyl; a 2 to 7 carbon organic acid ester or diester of —COCH$_2$OH, —CHOHCH$_2$OH, or —CHOHCH$_3$; or the groups —COCH$_2$OH, —CHOHCH$_2$OH, or —CHOHCH$_3$ having a 1 to 6 carbon alkyl or aryl ether replacement of one or more hydroxyls; or 13-ketimine derivatives of —COCH$_3$ or —COCH$_2$OH;
Y is methoxy, hydroxy, or hydrogen; and X is O or NH, but when Y is hydroxy or hydrogen, X must be O;
and wherein R' is a 1 to 3 carbon alkyl; and
or wherein Z is O, S, CH$_2$ or CHOR' wherein R' is 1 to 3 carbon alkyl,
and the pharmaceutically acceptable acid additive salts thereof; are useful for retarding tumor proliferation.

12 Claims, No Drawings
Microfiche Appendix Included
(04292003 Microfiche, Griffin; Ronald W. Pages)

BRIDGED OXYGEN ANALOGS OF DAUNORUBCIN AND DOXORUBICIN

SPONSORSHIP

The invention described herein was made in the course of work under National Cancer Institute Grant No. CA32250 of the Department of Health and Human Services.

REFERENCE TO RELATED APPLICATION

This a continuation in part of copending U.S. application Ser. No. 598,016, filed Apr. 9, 1984, now U.S. Pat. No. 4,585,859, which is a continuation in part of U.S. application Ser. No. 496,122, filed May 24, 1983, now U.S. Pat. No. 4,464,529, which is, in turn, a continuation in part of U.S. application Ser. No. 400,120, filed July 20, 1982, and now abandoned.

TECHNICAL FIELD

This invention is in the field of anthracycline chemistry. More particularly, it concerns analogs of doxorubicin and daunorubicin that are useful antitumor agents.

BACKGROUND ART

Doxorubicin (adriamycin) is widely used as an antitumor agent in the treatment of a wide range of solid tumors and leukemias. However, many patients with these tumors fail to respond and essentially no patients with some serious tumor types (colon cancer, melanoma) respond. In addition, in some patients chronic treatment produces irreversible heart damage that can be fatal if treatment is continued. Thus, there is continuing need for analogs which give a better rate of response, a wider spectrum of response, or reduced cardiotoxicity. Various analogs have been screened in a widely used test against mouse leukemia P388 and most have been found wanting. Others are useful, but do not provide a complete solution to the problem.

Much of the history and prior art of doxorubicin and its anthracycline analogs is found in the article "Adriamycin" by David W. Henry, *ACS Symposium Series, No. 30, Cancer Chemotherapy*, American Chemical Society, pp. 15–57 (1976) and in the book *Doxorubicin* By Frederico Arcamone, Acadamic Press, 1981.

Some specific analogs are of interest. N,N-dibenzyl-daunorubicin is disclosed in U.S. Pat. No. 4,035,566 (1977); 5-iminodaunorubicin in U.S. Pat. No. 4,109,076 (1978); the doxorubicin equivalent in E. Acton et al, *J Med Chem* (1981) 24: 669; and 3'-deamino-3'-(4-morpholinyl) daunorubicin in U.S. Pat. No. 4,301,277 (1981).

A general reductive alkylation process for preparing new semisynthetic anthracycline derivatives is described in Tong, G. L., et al, *J Med Chem* (1979) 22: 912–918. Piperidinyl and 4-methoxypiperidinyl derivatives are disclosed in U.S. Pat. Nos. 4,202,967 (1980) and 4,314,054 (1982). Cyanmorpholino analogs are disclosed in U.S. Pat. No. 4,464,529 (1984).

A group of bridged oxygen analogs was disclosed in U.S. Ser. No. 598,016, of which this is a continuation in part. The present application discloses further details related to a subclass of this group, the 4-alkoxy piperidinyl derivatives. The morpholino analogs are also described in Acton, E. M., et al, *J Med Chem* (1984) 27: 638.

The subject matter of this prior art is specifically incorporated herein by reference.

DISCLOSURE OF THE INVENTION

The compounds of the invention in one aspect are of the formula

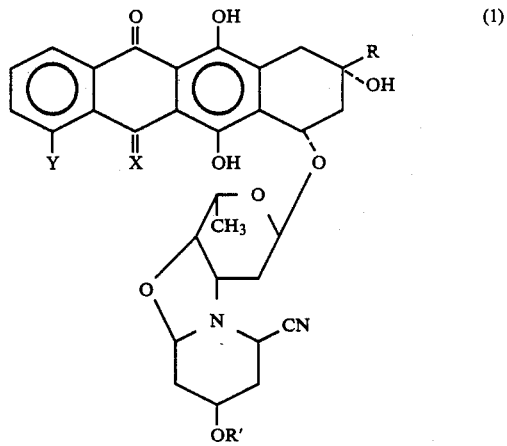

wherein
R is —COCH$_3$, —CHOHCH$_3$, —COCH$_2$OH, or —CHOHCH$_2$OH; hydrogen; hydroxyl; a 1 to 3 carbon alkyl; a 1 to 3 carbon ω-hydroxyalkyl; a 2 to 7 carbon organic acid ester or diester of —COCH$_2$OH, —CHOHCH$_2$OH, or —CHOHCH$_3$; or the groups —COCH$_2$OH, —CHOHCH$_2$OH, or —CHOHCH$_3$ having a 1 to 6 carbon alkyl or aryl ether replacement of one or more hydroxyls; or 13-ketimine derivatives of —COCH$_3$ or —COCH$_2$OH;

Y is methoxy, hydroxy, or hydrogen; and X is O or NH, but when Y is hydroxy or hydrogen, X must be O;

and wherein R' is a 1 to 3 carbon alkyl.

In another aspect, the invention relates to compounds of the formula

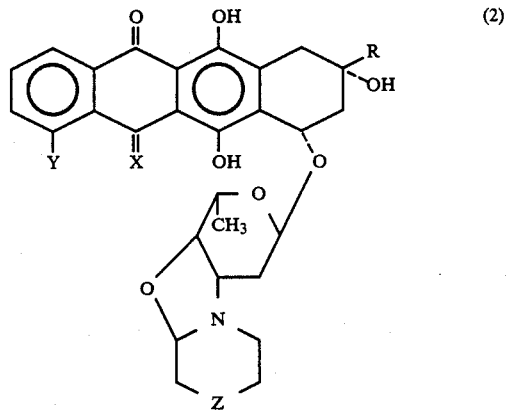

wherein
R, X and Y are as above defined, and Z is O, S, CH$_2$ or CHOR', wherein R' is a 1 to 3 carbon alkyl;
and the pharmaceutically acceptable acid addition salts thereof.

In other aspects, this invention provides pharmaceutical preparations containing the compounds of the invention as well as a method for treating mammalian tumors by administering such preparations. It also relates to a process for preparing the compounds of the invention.

MODES OF CARRYING OUT THE INVENTION

The compounds of the invention contain at least two chiral centers and those which contain CN in a 4-alkoxyl piperidine ring contain at least three chiral centers which do not exist in daunorubicin or doxorubicin per se, and therefore wherein the configuration is unspecified. Accordingly, the compounds of the invention exist in diastereomeric forms, which, of course, may be separated using conventional techniques for separation of compounds in general, such as chromatography, selective crystallization, and the like. The invention includes all such individual diastereomers, as well as mixtures thereof. However, certain diastereomeric mixtures are preferred, as set forth below.

DERIVATIVES AND ANALOGS

The compounds of the invention can also be present as, for example, ester, ether, or ketimine derivatives. These derivatives are formed so as to increase the solubility of the compounds or so as to vary other physical properties of the compounds.

The derivatives can be prepared from daunorubicin or doxorubicin and converted to the compounds of the invention as described below.

One or more of any hdyroxyls of R may be esterified with a 2-7 carbon organic acid, including alkanoic acids, oxyalkanoic acids, hydroxyalkanoic acids, and benzoic acid. Exemplary are esters of acetic acid, propionic acid, glycolic acid, benzoic acid, and of more complex acids such as HOOC—CH(OC$_2$H$_5$)$_2$.

Such esters of doxorubicin, are described in Arcamone et al, *J Med Chem* (1974) 17: 335, and Maral et al, French Pat. No. 848,219 (May 10, 1977) and are prepared as there described.

In addition, one or more of any hdyroxyls present in R can be present as ethers—particularly 1 to 6 carbon alkyl esters, for example the methyl ether, ethyl ether, butyl ether, or phenyl ether. Such 14-ethers of doxorubicin have been described in Masi et al, *Il Farmaco, Ed. Sci.,* (1979) 34: 907.

The 4-demethoxy analogs of doxorubicin and daunorubicin (no CH$_3$O in A-ring of the aglycone) are readily obtained (Arcamone et al, *Cancer Test Rpts* (1976) 60: 829; Arcamone et al, German Pat. No. 2,652,391 (May 26, 1977)) and converted to compounds of this invention.

The carbonyl groups in R of daunorubicin and doxorubicin can be readily converted to ketimine groups by the common methods for converting ketones to oximes, hydrazones, and other ketimines. Exemplary are the derivatives —C(NOH)—CH$_2$OH, —C(NOH)—CH$_3$, —C(NOCH$_3$)—CH$_2$OH, —C(NOCH$_3$)—CH$_3$, —C(NNHCOC$_6$H$_5$)—CH$_2$OH, —C(NNHCOC$_6$H$_5$)—CH$_3$, —C(NNHCONH$_2$)CH$_2$OH, —C(NNHCONH$_2$)—CH$_3$, and the like.

The R unit can also be simplified to convert R to, for example, —OH, —CH$_2$OH, or —C$_2$H$_4$OH. (See Penco et al, German Pat. No. 2757057 (1978); Penco et al, *J Antibiotics* (1977) 30: 764.)

The 5-imino compounds can be easily and directly prepared from daunorubicin and doxorubicin using the methods disclosed in Tong, G., et al, *J Med Chem* (1979) 22: 36 and in Acton, E. A., et al, *J Med Chem* (1981) 24: 669. The 5-oxo materials are contacted with an excess of alcoholic ammonia at low to moderate temperatures such as from −25° C. to +25° C. for from about 0.5 to about 100 hours. In the case of hydroxyl-containing analogs, it is necessary to block free hydroxyl before the ammonia treatment, using a mild acid-labile protecting group such as methoxy-trityl. The trityl functionally can be introduced by treating the analog with excess p-anisyl chlorodiphenylmethane at room temperature or the like. After the reaction with ammonia is complete, the hydroxyl can be regenerated by contact with acid such as acetic acid or cold aqueous trifluoroacetic acid.

All of these derivatives of daunorubicin or doxorubicin can be readily converted to compounds of this invention by the reductive alkylation procedures described below.

The compounds of the invention which do not contain CN in the piperidinyl, morpholino or thiomorpholino ring are prepared as the free base or as the pharmaceutically acceptable acid addition salts. (The compounds of the invention wherein —CN is adjacent the ring N do not, apparently, form acid addition salts, as the electron withdrawing effect of the cyano group destroys the basicity of the ring nitrogen.)

"Pharmaceutically acceptable" salts are nontoxic and generally employed in pharmaceutical products. Examples are salts of inorganic acids, such as hydrochloric, hydrobromic, sulfuric, and phosphoric acids, and of organic acids such as acetic, glycolic, maleic, maleic, hydroxymaleic, tartaric, citric, salicyclic, methanesulfonic, and p-toluenesulfonic acid. Mixtures of two or more acid addition salts may be used, as may mixtures of the free base plus one or more acid addition salts. For reasons of simplicity and ready solubility, the hydrochloric and hydrobromic acid addition salts are preferred.

Preparation of the Bridged Oxygen Analogs

The compounds of the invention can be prepared in general as follows.

For compounds containing the 4-alkoxy piperidinyl moiety, an adriamycin analog, such as commercially available daunorubicin or doxorubicin (as an acid addition salt) or a derivative as described above is reacted under reductive alkylation conditions with a compound of the formula

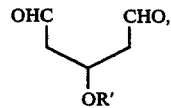

wherein R' is methyl, ethyl, n-propyl, or i-propyl. The starting dialdehyde is prepared by oxidation of the corresponding cyclic diol of the formula

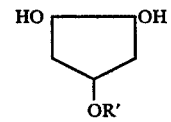

which is, in turn, prepared from the corresponding 4-alkoxycyclopentene in a manner described by Ray, R., et al, *Tett Lett* (1980) 21: 449. The cyclopentene derivative is obtained by alkylation of 4-hydroxycyclo pentene in a procedure described by Fleming, I., et al, *Tetrahedron* (1972) 28: 4989; the 4-hydroxycyclopentene itself is prepared as described by Allred, E. L., et al, *J Org Chem* (1960) 25: 26.

For compounds wherein Z is CH$_2$, the dialdehyde is prepared as above, except that cyclopentene itself is used as a starting material. If Z is O or S, the corresponding dialdehyde is prepared by acid hydrolysis of

or its thio analog by the method of Belgian Pat. No. 655,436, or by cleavage of

or its thio analog as described by Barry, et al, *Carbo Res* (1968) 7: 299 or by Greenberg, et al, *Carbo Res* (1974) 35: 145.

The alkylation is conducted using an excess of the dialdehyde in a mixed aqueous polar organic medium such as water/acetonitrile, generally at a pH of about 6. For the compounds of Formula 1, containing both a cyano and bridged oxygen group, the alkylation is conducted in the presence of sodium cyanide. Reductive alkylation in the presence only of a cyano-group-containing reducing agent such as sodium or potassium cyanoborohydride results in the formation of some of this product; however, larger amounts of corresponding compounds lacking either or both the cyano and bridged oxygen groups are also obtained. For preparation of the bridged oxygen compounds of the invention of Formula 2 which lack a CN group, therefore, it is preferred that only the reducing agent be present. For the compounds of Formula 1 the reaction is most preferably conducted using only the dialdehyde, the adriamycin analog substrate, and about a 1–3 molar excess of sodium cyanide. The alkylation can also be conducted in the presence of both sodium cyanide and the cyano-containing reducing agents. (When reducing agent is present any carbonyl groups in R may also be reduced.)

The reaction time is relatively short, of the order of 15 minutes, and for production of the bridged oxygen products, this shorter reaction time is preferred. A reductive alkylation of this general type is also shown in U.S. Pat. Nos. 4,301,277, 4,202,967, 4,314,054, and in *J Med Chem* (1982) 25: 18–24.

Alkylation in the presence of reducing agent yields a mixed product containing four principal components, including products containing the reduced form of any carbonyl moieties in R. If NaCN alone is used, this side chain reduction does not occur. In the case of daunorubicin, for example, using a 3-alkoxy (R'O) dialdehyde, where R' is methyl, these components are:

3'-deamino-3'-(4"-methoxypiperidinyl) daunorubicin,
3'-deamino-3'-(4"-methoxypiperidinyl)-13-dihydro dauno rubicin,
3'-deamino-3'-(2"-cyano-4"-methoxypiperidinyl)-dauno rubicin, and
3'-deamino-3'-(2"-cyano-4"-methoxypiperidinyl)-13-dihydro daunorubicin;

corresponding products are obtained for doxorubicin.

However, smaller amounts of the 2"-hydroxyl and 6"-hydroxyl-2"-cyano derivatives are also obtained, leading to the formation of the bridged oxygen compounds of the invention, which are isolated from the reaction mixture.

Corresponding smaller amounts of the 2"-hydroxy derivatives of the piperidinyl, morpholino or thiomorpholino analogs result in the bridged oxygen compounds of Formula 2.

Acid extraction of the reaction product from the alkylation is effective to separate the acid-extractable noncyano-substituted materials (wherein the ring nitrogen retains its basicity) from the acid-insoluble cyano-substituted materials. However, some of the compounds of Formula 2 fail to extract in this fraction due to their overall hydrophobicity.

The neutral product fraction from these reactions, which remains in the organic layer after extraction with aqueous acid, contains the corresponding 2"-cyano-4"-methoxypiperidinyl derivatives of daunorubicin and doxorubicin, including products with 6"-hydroxy substitutions. It also contains, for the reason stated above, some of the 2"-hydroxy substituted morpholino, thiomorpholino, and piperidinyl derivatives.

The resulting extracts can then be separated into individual compounds or stereoisomeric mixtures by various chromatographic methods such as preparative layer chromatography, column chromatography, or preparative high performance liquid chromatography.

Using column chromatography, the bridged oxygen-containing compounds of the invention are obtained by isolating the desired fraction. The position of elution of this fraction varies, of course, with the chromatography support and eluting mechanism. Particular procedures are illustrated below, but general art-recognized methods can be adapted to the isolation of the compounds of the invention. In general, a silica gel adsorbent is effective to separate the derivatives in the manner described. While precise elution positions vary with conditions and with specific adsorbent choice, for compounds within the same general class, such as those produced in the preparations described herein and exemplified below, will exhibit similar behavior when reasonable similarity of chromatography conditions is maintained. That is, for adsorbents of the same general class (such as silica gels) and for elution gradients in the same direction (such as increasing polarity), the same relative elution positions for members of the class results. Therefore, using the examples below, modified separations are predictable as to the order of elution of the desired components.

Utility and Administration

The compounds of the invention are antitumor agents (see Example 5). For this use, the compounds, including the salts, can be administered by any available route, including oral and parenteral (intravenous, intraperitoneal, subcutaneous, and intramuscular) administration. Parenteral administration, especially intravenous administration, has historically been the mode of choice. The dosing regimen and amount administered is, of course, dependent on the subject, the severity of the condition, and the judgment of the physician. For example, in the treatment of test animals, a dosage of about 0.0010 mg/kg to about 25 mg/kg per day is sufficient to ameliorate leukemia. The upper dosage limit is that imposed by toxic side effects and can be determined by trial and error for the animal to be treated. In general, the dosage with compounds of this invention will be lower than (e.g., 1/20 to 1/200 times) that required with the parent compounds. Dosing regimens of one dose every 2 to 7 days are effective, but shorter intervals between dosings may be used as well.

To facilitate administration, the compounds of this invention, including the salts, are provided in pharmaceutical composition form, and preferably in unit dosage form. While the compounds can be administered per se, it is more common to administer them in conjunction with a pharmaceutically acceptable carrier which dilutes the compound and facilitates handling. The term "pharmaceutically acceptable" means that the carrier (as well as the resulting composition) is sterile and nontoxic.

For oral dosage, the carrier or diluent can be solid, semisolid, or liquid, and can serve as a vehicle, excipient, or medium for the agent as described in pharmacology texts. For parenteral administration, the compound is dissolved or suspended in a suitable injectable liquid medium as is known in the art.

In the preparation of these dosage forms, one can use the art-accepted techniques for formulating water soluble pharmaceutical agents (in the case of salts) and water insoluble agents (in the case of the free bases).

The examples illustrate the invention and are not to be construed as limiting its scope.

Example 1

Preparation, Isolation, and Identification of 3'-deamino-6″,4'-anhydro-(2″-cyano-6″-hydroxy-4″-methoxypiperidinyl) doxorubicin Stereoisomers Reductive Alkylation Solid sodium periodate (9.63 g, 45.0 mmol) was added to a stirred solution containing 7.450 g (56.3 mmol) of 4-methoxy-1,2-cyclopentanediol in 100 ml of water that was colled in a water bath at about 15° C. The slightly turbid solution that results was stirred at room temperature in the dark for 15 hr. A 2 μl aliquot was removed from the solution and the presence of dialdehyde was confirmed using TLC. After 17 hr, the dialdehyde solution, pH 3.20, was adjusted to pH 6.0 with sodium bicarbonate and then diluted with 120 ml of acetonitrile. A large amount of precipitate formed.

The cold mixture was warmed to room temperature and stirred vigorously, and a solution containing 0.221 g (4.5 mmol) of sodium cyanide in 4.6 ml of 1N acetic acid (solution=pH 6.0), a solution of 0.283 g (4.5 mmol) of sodium cyanoborohydride in 6 ml of acetonitrile:$H_2O$ (1:1), and a solution of 2.610 g (4.5 mmol) of doxorubicin in 70 ml of the same solvent were added. The solution was stirred at room temperature in the dark for 5 min and a 2 μl aliquot was removed from the solution for analysis by TLC. After 15 min of reaction time, the reaction was poured into 100 ml of dilute sodium bicarbonate and the mixture was extracted with chloroform (4×75 ml). The combined organic phase was washed with water, adjusted to pH 7 with sodium bicarbonate (2×100 ml) and the resulting emulsion back-extracted with 3×5 ml chloroform, the chloroform extracts dried over sodium sulfate, filtered through Celite ™.

The filtrate was evaporated under vacuum and the residue dissolved in 25 ml methylene chloride, and 50 ml ether was added dropwise with stirring. The mixture was evaporated under vacuum to afford a red semisolid residue of 3.840 g, that was triturated with 25 ml ether and the resultant precipitate was collected, washed with ether (4×25 ml) and dried at room temperature in the dark to obtain 2.870 g of a dark red powder. Thin layer chromatography of the powder showed it to contain at least 10 components.

Preparation of the Neutral Extract

A 3.339 g sample of this crude mixture (prepared as described above in two separate alkylations) was dissolved in 250 ml chloroform and the solution extracted with 5×50 ml of 0.1N acetic acid, 50 ml water, and 50 ml of dilute sodium bicarbonate solution. The organic phase was dried over sodium sulfate, filtered through Celite ™, and evaporated under vacuum. The residue was dissolved in 15 ml methylene chloride, and the solution was diluted with 50 ml ether added dropwise with stirring. The resulting mixture was evaporated and dried at room temperature under vacuum to afford a red semisolid residue of 1.374 g containing the neutral products of the reaction.

The basic components can be, if desired, recovered from the acid extract above.

Characterization of the Neutral Extract

The neutral extract was shown by TLC (using chloroform:methanol, 29:1) to contain a variety of components. To separate them, a 1.363 g sample of this mixture in 5 ml of methylene chloride was applied to a 1.9×53 cm column containing silica gel prepared from 69 g of Bio-Rad Biosil-A 200–400 mesh silica gel, packed and washed with methylene chloride. The column was eluted using a shallow gradient of methanol in methylene chloride. The elution protocol is shown below:

| Fraction No. | Vol (ml) | Solvent |
| --- | --- | --- |
| 1–30 | 300 | $CH_2Cl_2$ |
| 31–80 | 500 | $CH_2Cl_2$:MeOH, 99:1 |
| 81–130 | 500 | $CH_2Cl_2$:MeOH, 98:2 |
| 131–330 | 2000 | $CH_2Cl_2$:MeOH, 97:3 |
| 331–350 | 200 | $CH_2Cl_2$:MeOH, 95:5 |
| 351–380 | 300 | $CH_2Cl_2$:MeOH, 90:10 |

The bridged oxygen compound of the invention wherein R is $COCH_2OH$ appeared in fractions 96–105 and 108–110, eluting in methylene chloride:methanol 98:2. These two fractions contained differing diastereomeric mixtures of this compound of Formula 1. The corresponding materials having the reduced form of R (—$CHOHCH_2OH$) eluted elsewhere, in fractions 163–198.

The alkylation reaction generates compounds having three chiral centers of unpredetermined configuration. Therefore, there are at least 8 theoretical stereoisomers of the title compound. These isomers were characterized by behavior on HPLC and TLC, and in no instance was it possible to assign any absolute configuration to the chiral centers. Six of the 8 stereoisomers were found on elution of HPLC, and were arbitrarily designated A, B, C, D, E, and F.

The material eluting in fractions 96–105 contained isomers B, C, D, and E in amounts of 0.9% B, 1.6% C, 25.7%D, and 71.8%E. The material eluting in fractions 108–110 was comprised primarily of isomers A and B (54%A, 40.3%B, and the remainder D and E). These fractions were characterized by thin-layer chromatography using chloroform-methanol at 29:1 and 19:1, with the results shown below:

| | Chloroform:MeOH | |
| --- | --- | --- |
| | 29:1 | 19:1 |
| Fractions 96–105 (D/E) | $R_f$ 0.50 | $R_f$ 0.58 |

-continued

| | Chloroform:MeOH | |
|---|---|---|
| | 29:1 | 19:1 |
| Fractions 108–110 (A/B) | $R_f$ 0.40 | $R_f$ 0.50 |

Characterization of the Silica Gel Column Fractions

The material in fractions 96–105 was triturated with ether to afford the predominantly D/E mixture of the title compound and was charactertized as follows: HPLC analysis on a Waters Radial-Park Nova C-18 5μ column with 0.1M $NaH_2PO_4$—$CH_2CN$ (65:35) at 2 ml/minute with 254 nm UV detection showed 0.6% C (23.5 min), 24.6% D (25.7 min) and 73.7% E (29.0 min). NDCI-MS (negative desorption chemical-ionization mass spectrum) m/e 664 (the title compound), 637 (the title compound minus HCN).

UV-Vis: 232 nm ($\epsilon$=38,500); 250 (26,300), 287 (9150), 477 (12,400), 494 (12,300), 530 (6810).

Elemental anal: Calculated for $C_{34}H_{36}N_2O_{12} \cdot \frac{1}{2}H_2O$; C: 60.62; H: 5.54; N: 4.16. Found: C: 60.46; H: 5.76; N: 4.10.

The material in fractions 108–110 was triturated with ether to yield the predominantly A/B isomers of the title compound and was characterized as follows: HPLC analysis (as above) showed 53.2% A (21.4 min), 44.0% B (22.1 min), 0.8% D (25.8 min), and 0.6% E (29.1 min). NDCI-MS m/e 664 (the title compound), 637 (the title compound minus HCN).

UV-Vis: 232 nm ($\epsilon$=38,100); 250 (26,000), 287 (8950), 477 (12,400), 494 (12,400), 530 (6850).

Elemental anal: Calculated for $C_{34}H_{36}N_2O_{12} \cdot H_2O$: C: 59.82; H: 5.61; N: 4.10. Found: C: 59.57; H: 5.50; N: 4.07.

Example 2

Preparation of 3′-Deamino-4′,2″-anhydro-3′-(2‴-hydroxy-4‴-morpholino) doxorubicin To a stirred solution of 6.25 g (60.0 mmol) of 1,4-anhydroerythritol in 75 ml water cooled to 15°–20° C., was added 6.42 g (30 mmol) of sodium metaperiodate. The resulting clear solution was stirred at room temperature for 17 hr. The solution pH was adjusted from 4.0 to 7.3 with $NaHCO_3$ and then diluted with stirring with 75 ml of $CH_3CN$. A precipitate formed. The mixture was stirred and 0.126 g (2.0 mmol) of $NaBH_3CN$ in 5 ml of 1:1 (vol) $CH_3CN$—$H_2O$ was added. To this mixture was then added 1.16 g (2.0 mmol) of doxorubicin hydrochloride in 30 ml of 1:1 $CH_3CN$—$H_2O$. After 10 min the reaction mixture was diluted with 50 ml of dilute $NaHCO_3$ and extracted three times with 50 ml portions of $CHCl_3$. Combined extracts were extracted with 0.1N acetic acid (5×25 ml) and then with $H_2O$ and washed with dilute NaH—$CO_3$ and saturated aqueous NaCl. The acidic aqueous phase was retained. The chloroform phase was dried over $Na_2SO_4$, filtered through Celite TM diatomaceous earth and concentrated to yield a residue. This residue was dissolved in 25 ml of $CHCl_3$ and solvent re-evaporated under vacuum at room temperature. This afforded 0.518 g (40%) of a dark red foamed glass.

A 0.424 g sample of this foamed glass material was dissolved in 1.5 ml of $CH_2Cl_2$ and applied on a 1.5×35.5 cm column of $CH_2Cl_2$-washed 200–400 mesh Bio-Sil A Silica gel. The column was eluted with $CH_2Cl_2$ (50 ml) and then $CH_2Cl_2$:$CH_3OH$ (99:1, 150 ml; 98:2, 150 ml; 97:3, 300 ml; 95:5, 100 ml and 90:10, 300 ml. The fraction eluting at approximately 400 ml, or at about 3% $CH_3OH$, is a mixture of 3′-deamino-3′-(2‴-cyano-4‴-morpholino)doxorubicin and title compound.

An 80 mg sample of this mixture was purified by preparative TLC on a 2 mm 20×20 cm silica gel plate in $CHCl_3$:$CH_2OH$ (19:1) to obtain 10.7 mg of $R_f$ 0.42. Trituration of the eluted spot with methanol gave 9 mg of title compound.

The product title compound was analyzed by HPLC on a Waters Radial Pak Nova C-18 5μ column with 0.1M $NaH_2PO_4$—$CH_3CH$ (65:35) at 2 ml/min with 254 nm UV detection gave a fraction with 85% title compound (30.4 min). NDCI-MS m/e 611; UV-Vis maximum ($CH_3OH$) 234 nm ($\epsilon$=33,200), 249 (21,200), 288 (8,140), 482 (9.970), 492 (9,930), 530 (6,440).

Example 3

Preparation of Acid Addition Salt

The free base product of Example 3 is suspended in 20 ml of water. The mixture is stirred and 3.2 ml of 0.1N HCl slowly added to give a pH of 4.5. The suspended solid gradually dissolves, and the solution is lyophilized in the dark to give the acid addition salt 3′-deamino-4′,2″-anhydro-3′-(2‴-hydroxy-4‴-morpholino)-doxorubicin hydrochloride.

Example 4

The preparations of Example 1 are repeated using, in place of doxorubicin as starting material, daunorubicin or a member included in the range of derivatized doxorubicins and daunorubicins described in the section denominated "Derivatives and Analogs".

Example 5

The compounds of this invention have utility as mammalian antitumor agents. This activity is evidenced by in vivo and in vitro studies. In one in vivo test, conducted in accordance with the protocol described in *Cancer Chemotherapy Reports, National Cancer Institute*, 3:2, Part 3 (September 1972), healthy mice were inoculated i.p. with lymphocyte leukemia P-388 ascitic fluid. The inoculated mice were then treated on days 5, 9, and 13 of the succeeding period with various amounts of compounds of the invention. As comparisons, other mice were untreated and additional mice were treated with daunorubicin or doxorubicin.

The average survival time for the various treated mice was determined and compared with that of the mice inoculated with the luekemia ascitic fluid but given not treatment with the test compounds. The data so obtained are shown below as % T/C values. % T/C represents the survival time of the treated mice divided by the survival time of the controls multiplied by 100. Dosage levels are also shown.

TABLE A

| | Activity vs Leukemia P-388 in Mice | |
|---|---|---|
| Compound | Survival Time % T/C | Optimum Dose (q4d 5,9,13) mg/kg |
| Doxorubicin | 252 | 7.5 |
| 3′-deamino-4′,6″-anhydro-3′-(2″-cyano-6″-hydroxy-4″-methoxy piperidinyl) doxorubicin A/B | 298 | 2.5 |
| 3′-deamino-4′,6″-anhydro-(2″-cyano-6″-hydroxy-4″-methoxy | 161 | 10.0 |

TABLE A-continued

| Compound | Activity vs Leukemia P-388 in Mice | |
|---|---|---|
| | Survival Time % T/C | Optimum Dose (q4d 5,9,13) mg/kg |
| piperidinyl) daunorubicin D/E | | |

These results demonstrate comparable activity to that shown by doxorubicin.

In an in vitro test, compounds were assessed for their ability to inhibit DNA/RNA synthesis in L1210 cells by the method of Tong, C., et al, *J Med Chem* (1976) 19: 395. 3'-Deamino-4',2''-anhydro-3'-(2''-hydroxy-4''-morpholino) doxorubicin gave $ED_{50}$ values of 0.031 μM and 0.0047 μM for DNA and RNA synthesis respectively; the corresponding values for doxorubicin were 1.5 and 0.58 μM. Therefore this compound of the invention is greatly more effective than doxorubicin in this test.

Example 6

Sterile Suspension in Aqueous Vehicle for Injection

| | Mg |
|---|---|
| Active ingredient | 3 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Example 7

Tablet Formulation

| | Mg |
|---|---|
| Active ingredient | 5.0 |
| Lactose | 91 |
| Cornstarch (dried) | 51.5 |
| Gelatin | 2.5 |
| Magnesium stearate | 1.0 |

The active ingredient is powdered and passed through a mesh sieve and well mixed with the lactose and 30 mg of the cornstarch, both passed through a sieve.

The mixed powders are massed with a warm gelatin solution, prepared for stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

Example 8

Capsules

| | Mg |
|---|---|
| Active ingredient | 10 |
| Lactose | 190 |

The active ingredient and the lactose are passed through a sieve and the powders well mixed together before filling into harde gelatin capsules of suitable size, so that each capsule contains 2000 mg of mixed powders.

We claim:

1. A compound of the formula

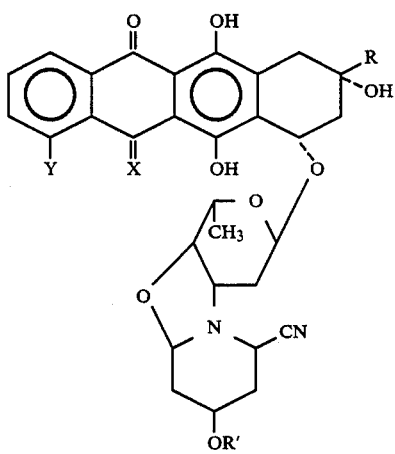

wherein
R is selected from the group consisting of —COCH₃, —CHOHCH₃, —COCH₂OH, —CHOHCH₂OH, hydrogen, hydroxyl, a 1 to 3 carbon alkyl, a 1 to 3 carbon ω-hydroxyalkyl, a 2 to 7 carbon organic acid ester or diester of —COCH₂OH, —CHOHC-H₂OH, or —CHOHCH₃; the groups —COCH₂OH, —CHOHCH₂OH, or —CHOHCH₃ having a 1 to 6 carbon alkyl or aryl ether replacement of one or more hydroxyls; 13-ketimine derivatives of —COCH₃ or —COCH₂OH;

Y is methoxy, hydroxy, or hydrogen; and X is O or NH, with the proviso that when Y is hydroxy or hydrogen, X must be O;

and wherein R' is a 1 to 3 carbon alkyl.

2. The compound of claim 1 wherein R is COCH₃, COCH₂OH, —CHOHCH₃, or —CHOHCH₂OH.

3. The compound of claim 2 wherein R' is methyl.

4. The compound of claim 2 wherein X is O.

5. The compound of claim 4 which is 3'-deamino-4',6''-anhdyro-3'-(2''-cyano-6''-hydroxy-4''-methoxypiperidinyl) doxorubicin.

6. The compound of claim 4 which is 3'-deamino-4',6''-anhydro-3'-(2''-cyano-6''-hydroxy-4''-methoxypiperidinyl) daunorubicin.

7. A compound of the formula

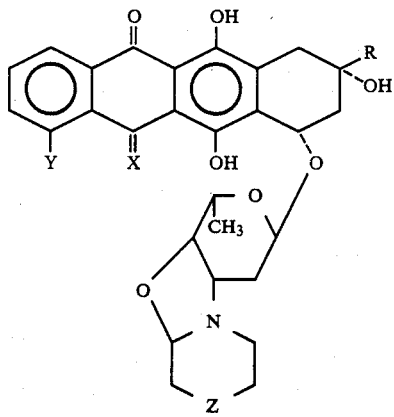

wherein
R is selected from the group consisting of —COCH$_3$, —CHOHCH$_3$, —COCH$_2$OH, —CHOHCH$_2$OH, hydrogen, hydroxyl, a 1 to 3 carbon alkyl, a 1 to 3 carbon ω-hydroxyalkyl, a 2 to 7 carbon organic acid ester or diester of —COCH$_2$OH, —CHOHCH$_2$OH, or —CHOHCH$_3$; the groups —COCH$_2$OH, —CHOHCH$_2$OH, or —CHOHCH$_3$ having a 1 to 6 carbon alkyl or aryl ether replacement of one or more hydroxyls; 13-ketimine derivatives of —COCH$_3$ or —COCH$_2$OH;

Y is methoxy, hydroxy, or hydrogen; and X is O or NH, with the proviso that when Y is hydroxy or hydrogen, X must be O;

and wherein Z is O, S, CH$_2$ or CHOR' wherein R' is 1 to 3 carbon alkyl, and the pharmaceutically acceptable acid additive salts thereof.

8. The compound of claim 7 wherein R is COCH$_3$, COCH$_2$OH, —CHOHCH$_3$, or —CHOHCH$_2$OH.

9. The compound of claim 8 wherein R' is methyl.

10. The compound of claim 8 wherein X is O.

11. The compound of claim 10 wherein Z is O.

12. The compound of claim 10 which is 3''-diamino-4',2''-anhydro-3'-(2''-hydroxy-4''-morpholino)doxorubicin.

* * * * *